United States Patent
Graβl

(10) Patent No.: US 8,361,107 B2
(45) Date of Patent: Jan. 29, 2013

(54) SPHYGMOMANOMETER CUFF FOR NON-INVASIVE BLOOD PRESSURE MEASUREMENT

(75) Inventor: Thomas Graβl, Lübeck (DE)

(73) Assignee: Dräger Medical GmbH, Lübeck (DE)

( * ) Notice: Subject to any disclaimer, the term of this patent is extended or adjusted under 35 U.S.C. 154(b) by 1237 days.

(21) Appl. No.: 12/170,679

(22) Filed: Jul. 10, 2008

(65) Prior Publication Data

US 2009/0043215 A1 Feb. 12, 2009

(30) Foreign Application Priority Data

Aug. 10, 2007 (DE) .......................... 10 2007 037 770

(51) Int. Cl.
*A61B 17/00* (2006.01)
*A61B 5/02* (2006.01)

(52) U.S. Cl. ........ 606/202; 606/201; 600/481; 600/485; 600/490; 600/499

(58) Field of Classification Search .................. 606/201, 606/202; 600/481, 485, 490, 499
See application file for complete search history.

(56) References Cited

U.S. PATENT DOCUMENTS

| | | | |
|---|---|---|---|
| 3,504,675 A | 4/1970 | Bishop | |
| 3,765,405 A | 10/1973 | Natkanski | |
| 4,901,732 A | 2/1990 | Williams | |
| 5,505,207 A | 4/1996 | Abbs et al. | |
| 5,660,182 A | 8/1997 | Kuroshaki et al. | |
| 5,733,304 A | 3/1998 | Spence | |
| 6,036,718 A * | 3/2000 | Ledford et al. | ............... 606/202 |
| 2006/0027946 A1 | 2/2006 | Kawamura | |

* cited by examiner

*Primary Examiner* — Stacy B. Chen
(74) *Attorney, Agent, or Firm* — McGlew and Tuttle, P.C.

(57) ABSTRACT

A sphygmomanometer cuff is provided for measuring the blood pressure over a blood vessel. The sphygmomanometer cuff has at least one inflatable cuff part (3), which can be filled with a fluid for exerting pressure on the blood vessel, wherein the inflatable cuff part (3) has different widths at at least two points (I, II) along its longitudinal direction.

19 Claims, 2 Drawing Sheets

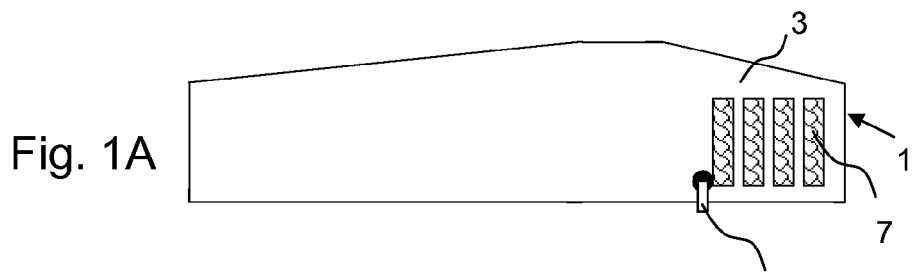
Fig. 1A
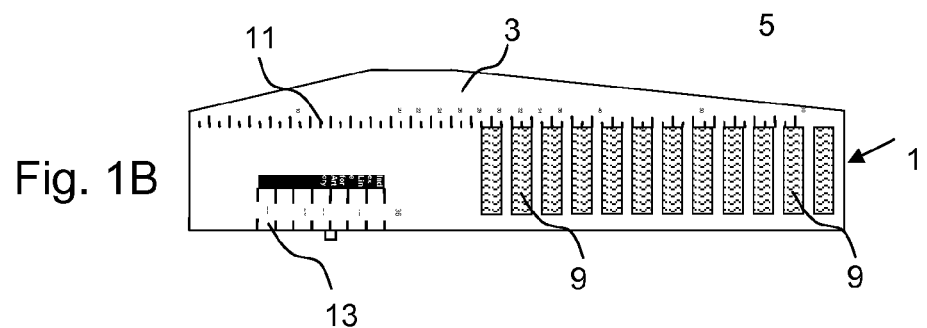
Fig. 1B
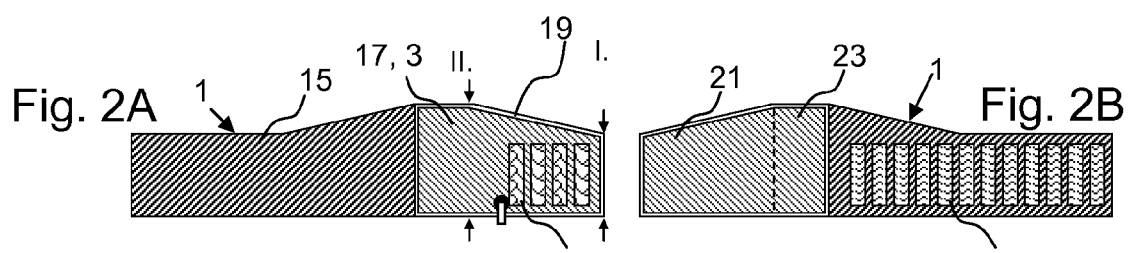
Fig. 2A | Fig. 2B
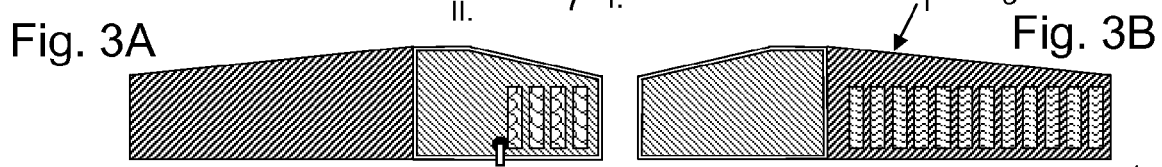
Fig. 3A | Fig. 3B
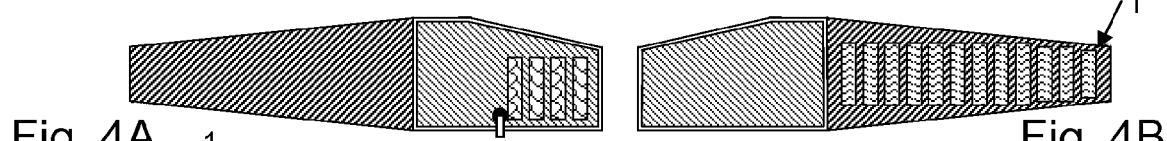
Fig. 4A | Fig. 4B
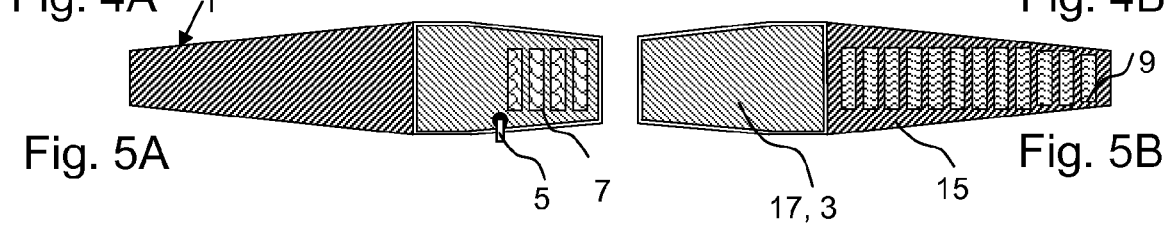
Fig. 5A | Fig. 5B

US 8,361,107 B2

SPHYGMOMANOMETER CUFF FOR NON-INVASIVE BLOOD PRESSURE MEASUREMENT

CROSS REFERENCE TO RELATED APPLICATIONS

This application claims the benefit of priority under 35 U.S.C. §119 of German Patent Application DE 10 2007 037 770.5 filed Aug. 10, 2007, the entire contents of which are incorporated herein by reference.

FIELD OF THE INVENTION

The present invention pertains to a sphygmomanometer cuff for measuring the blood pressure when applied over a blood vessel. The present invention pertains, furthermore, to a process for manufacturing a sphygmomanometer cuff.

BACKGROUND OF THE INVENTION

Sphygmomanometer cuffs for non-invasive or bloodless blood pressure measurement are known from practice. They usually have an elongated, rectangular cuff, which is placed around the upper arm, thigh or another body part of a patient in a ring-shaped pattern for measuring the patient's blood pressure and contain a rectangular inflatable cuff part. This inflatable cuff part may be filled with a fluid—usually air or gas—and presses a blood vessel located within the body part surrounded by the cuff, usually an artery, such that the flow sounds generated in the blood vessel due to the pressure applied to it make it possible to measure the blood pressure according to Riva-Rocci.

To determine the blood pressure as correctly as possible by means of a sphygmomanometer cuff as described above, special attention must be paid to ensure that the height of the inflatable cuff part over the blood vessel (i.e., the extension of the inflatable cuff part in the direction of blood flow in the blood vessel to which pressure is being applied by the inflatable cuff part) be equal to about 40% of the circumference of the body part on which the blood pressure measurement is being carried out. In case of blood pressure measurement on the upper arm of a patient, the inflatable cuff part extending in the longitudinal direction of the upper arm should therefore have a width or height that corresponds to 40% of the circumference of the upper arm.

Since there may be substantial differences among patients in terms of the circumference of their upper arm—as well as other body parts used for blood pressure measurement, and any other body part suitable for blood pressure measurement will also be meant therefore when referring to the upper arm below according to the present invention—various sizes of sphygmomanometer cuffs are available in specialist shops, as they are also disclosed, for example, in the German Patent Application DE 195 02 573 A1.

The circumference of, for example, the upper arm is often estimated only too approximately for selecting the corresponding size of cuff in the routine practice of blood pressure measurements. However, the incorrect cuff size selected on the basis of this erroneous estimation regularly leads to considerable errors of measurement, which has meanwhile been able to be demonstrated by a large number of studies. In the case in which the cuff selected is too small, so that the area over which the force acts due to the inflated inflatable cuff part is too small, the measured blood pressure is consequently incorrectly too high. If an excessively large cuff is used, whose force acts along an excessively large section of the artery, the measured blood pressure is consequently incorrectly too low. Even small deviations from the intended 40% of the circumference in selecting the sphygmomanometer cuff to be used may lead to considerable deviations of the measured blood pressure values. For example, a measured blood pressure that is too low by 10% can be seen, for example, in case of a sphygmomanometer cuff that has a width or height corresponding to a full 50% of the circumference of the upper arm instead of the desired 40%. Likewise, a sphygmomanometer cuff inflatable cuff part whose width or height is only 20% of the circumference of the upper arm leads to a measured blood pressure that is too high by 20%.

However, experience has shown that such errors of measurement also occur during the determination of the blood pressure when the actual upper arm circumference is known but the correct sphygmomanometer cuff was not available for the blood pressure measurement. Experience has shown that the blood pressure measurement is carried out in such cases with cuffs of an incorrect size that do not fit optimally.

Measurement of the blood pressure on the upper arm, for which the circumference of the upper arm is used to determine the suitable width or height of the inflatable cuff part, may lead to incorrect measurements as well. The applicant was able to determine that the "40% of the upper arm circumference" rule as an indicator for the height or width of the inflatable cuff part of the sphygmomanometer cuff does not lead to reliable measurement results for all patients. The correctly determined blood pressure consequently depends on the size of the sphygmomanometer cuff for the patient.

The sphygmomanometer cuffs known commercially, such as those known from DE 195 02 573 A1, are usually manufactured from a rectangular piece of fabric, which is coated with PU or PVC. This piece of material is cut to twice the size the finished cuff has during use and subsequently reduced by half by simple folding in one direction. The three open cuff edges formed as a result are sealed, and the inflatable cuff part is manufactured in the same step. The drawback of the manufacture of conventional sphygmomanometer cuffs as described above is that a needlessly large amount of coated material is used, which leads to higher costs than necessary.

SUMMARY OF THE INVENTION

The object of the present invention is to propose a cuff, by means of which improved blood pressure measurement can be carried out. In particular, it shall make possible measurements in the clinical routine practice with smaller errors of measurement than was hitherto common.

According to the invention, a sphygmomanometer cuff is provided for measuring the blood pressure by application over a blood vessel. The sphygmomanometer cuff comprises a cuff structure including an inflatable cuff part for being filled with a fluid for exerting pressure on the blood vessel. The inflatable cuff part has a first width at a first region or first point along a longitudinal direction of the inflatable cuff part and has a second width at a second region or second point along the longitudinal direction of the inflatable cuff part.

Thus, a sphygmomanometer cuff for measuring the blood pressure over a blood vessel, which has at least one inflatable cuff part, which can be filled with a fluid to exert pressure on the blood vessel, is proposed according to the present invention. The inflatable cuff part has different widths at at least two points along its longitudinal direction. This means that the inflatable cuff part has sections of different width, and it therefore extends to different heights along the blood vessel during use. The longitudinal direction of the inflatable cuff part according to the present invention corresponds to the circumferential direction around the body part around which the sphygmomanometer cuff is placed. The longitudinal direction of the inflatable cuff part thus comes to lie on the circumference of the body part, for example, the upper arm, in a ring-shaped or strip-shaped pattern when the sphygmomanometer cuff is being used. The blood vessel on which pressure is to be applied for the blood pressure measurement thus extends through the sphygmomanometer cuff applied in a ring-shaped or strip-shaped pattern during the use of the cuff.

A simple rotation of the sphygmomanometer cuff in the circumferential direction relative to the body part on which the blood pressure is being determined therefore causes sections of different widths of the inflatable cuff part to come to lie over the blood vessel and to press the blood vessel or to exert pressure on same over different lengths. Thus, it is advantageously possible when the sphygmomanometer cuff according to the present invention is used to correctly determine the blood pressure of at least two patients of different constitution and especially with different circumferences of the corresponding body part, for example, of the upper arm. The sphygmomanometer cuff according to the present invention is thus suitable for determining the blood pressure of patients with different constitutions. It can therefore combine in itself at least two, up to a plurality or multitude of sizes, as described in DE 195 02 573 A1.

The inflatable cuff part of the sphygmomanometer cuff according to the present invention may be designed here as an inflatable cuff part which is filled with air or another gas. However, provisions are also made according to the present invention for the inflatable cuff part to be able to be filled with a liquid or any other fluid.

An inflatable cuff part shall be defined according to the present invention not only as a fillable cavity or space. Any other arrangement within the sphygmomanometer cuff, which is suitable for selectively exerting pressure on a blood vessel for measuring the blood pressure—this may happen, for example, by means of a variable projection located over the blood vessel or a means for shortening the circumference of the sphygmomanometer cuff to increase the tension exerted by the sphygmomanometer cuff, for example, on the upper arm—is also defined as an inflatable cuff part according to the present invention.

The inflatable cuff part of the sphygmomanometer cuff according to the present invention may be divided, furthermore, in any embodiment of the inflatable cuff part, into individual segments. Thus, it is not necessary according to the present invention for the inflatable cuff part to be a one-piece inflatable cuff part that is continuous in the longitudinal direction. A plurality of "partial" inflatable cuff parts arranged in the sphygmomanometer cuff, which are of different widths—and optionally operate according to different mechanisms on the basis of which pressure is exerted—are also defined as inflatable cuff part according to the present invention and are therefore also covered by the present invention.

Since the inflatable cuff part of the sphygmomanometer cuff according to the present invention has at least two different widths along its longitudinal direction and may, moreover, have a plurality of different widths or heights, it is ensured that all necessary sphygmomanometer cuff sizes can be covered in a combined form in one sphygmomanometer cuff according to the present invention. In particular, intermediate sizes, which precisely are not covered by the conventional sizes, are advantageously also covered by the sphygmomanometer cuff according to the present invention.

Moreover, it is advantageous that it cannot happen during the use of a sphygmomanometer cuff according to the present invention that nearly all sphygmomanometer cuff sizes would be available in the hospital or the office but the size that is indeed suitable is not available. The sphygmomanometer cuff according to the present invention is therefore suitable, for the reasons mentioned above, for counteracting the development of errors of measurement during blood pressure measurement.

Thus, in a preferred embodiment according to the present invention, the sphygmomanometer cuff has an inflatable cuff part that comprises a conical section. An inflatable cuff part with a conical section is comparatively simple and can be manufactured at a low manufacturing effort and therefore at low cost. Furthermore, it makes possible the correct measurement of blood pressure even in patients who would need a sphygmomanometer cuff in the range of the above-mentioned "intermediate size." The provision of a conical inflatable cuff part therefore corresponds to the provision of a plurality of inflatable cuff parts of different heights or widths.

The provision of a blood vessel mark on the sphygmomanometer cuff according to the present invention of another preferred embodiment facilitates the correct placement of the sphygmomanometer cuff. In addition to the mark for the blood vessel, the sphygmomanometer cuff may have, furthermore, a scale with size indication in another preferred embodiment according to the present invention, the size indication being able to be related to a measured circumference of the body part or length of a body part, for example, a measured upper arm length (as will be discussed in detail below). This advantageously facilitates the accurate determination of the relevant circumference or of the relevant length without using an additional aid or tool. Using the sphygmomanometer cuff according to the present invention alone and without additional aids, it is thus additionally also possible to determine the width over which the inflatable cuff part of the sphygmomanometer cuff shall exert pressure on the blood vessel.

In another preferred embodiment, the sphygmomanometer cuff according to the present invention has a section, in which the cuff has no inflatable cuff part, and which extends conically. This shape makes possible the optimal adaptation of the sphygmomanometer cuff to patients with different upper arm lengths or upper arm circumference. The angle that is obtained due to the conical shape is preferably between 5° and 20° in relation to the longitudinal direction of the inflatable cuff part or in relation to the circumferential direction of the upper arm or of the body part in general. The angle especially preferably equals 15°.

In yet another preferred embodiment, the sphygmomanometer cuff according to the present invention has an axially symmetrical shape. This special geometric shape leads to improved ergonomics above all in the operating room because it also permits the sphygmomanometer cuff to be put on from the head side of the patient. The flexible tube can thus also leave the sphygmomanometer cuff on the head side. The anesthesiologist located in the head area of the patient is thus optimally able to use the sphygmomanometer cuff as well. Furthermore, any type of lettering may be arranged for this purpose (e.g., scale indications, the length indications as well as the artery or vessel mark) on the cuff at right angles to the longitudinal direction or such that it can also be read from the cranial direction or from the cranial as well as caudal directions.

The sphygmomanometer cuff, which usually has a closing device for being closed, may have a plurality of closing devices divided into a plurality of closing means (closing elements) in another preferred embodiment according to the present invention. As a result, the flexibility of the sphygmomanometer cuff is increased in terms of its curvature around the body part or the upper arm. Sharp corners, which are formed in an uncontrolled manner especially when the inflatable cuff part is being filled at sites at which the conventional cuffs are kinked above all in the inflated state, are advantageously prevented from forming in this embodiment according to the present invention. This division is possible not only in case of a Velcro® type (hook and loop) closure used as a closing device, but also in any other manner of closing the cuff. These manners include especially hooks and eyelets or bonded or adhesive closures.

Thus, a process for manufacturing a sphygmomanometer cuff, which process comprises the fluid-tight assembly of two material layers, which have different widths at at least two points along their longitudinal direction, is proposed according to the present invention. All the advantages already discussed above can be gained to the full extent with the sphygmomanometer cuff manufactured according to this process according to the present invention for manufacturing a sphygmomanometer cuff and according to its variants according to the present invention. Reference is therefore explicitly made here to the above discussion of these advantages to avoid repetitions.

In another preferred embodiment, the inflatable cuff part is formed between two layers of cuff material such that another section of the sphygmomanometer cuff, which section has no inflatable cuff part, has only one layer of cuff material. Unlike in the case of the doubling of the material known from the state of the art, as was described in the introduction, the starting material for making the sphygmomanometer cuff is cut such that after folding and sealing of the open edges formed in the process, the sphygmomanometer cuff has a double layer of material in the area of the inflatable cuff part only. This advantageously contributes to a reduction of the costs, because the cuff material, which is used as a single layer only rather than as a double layer in the embodiment being discussed here in the sections of the sphygmomanometer cuff that carry no inflatable cuff part, is relatively expensive. This procedure is therefore used to save material and therefore to reduce the costs in the manufacture of the sphygmomanometer cuff according to the present invention.

In an especially preferred embodiment of the process according to the present invention, the inflatable cuff part is limited by a cuff material as well as a film material, which differs therefrom, and is designed in this manner. A double layer of the cuff material, i.e., of the material of which the inflatable cuff part is manufactured, may be absent here altogether. The second layer of material needed to complement the inflatable cuff part may consist, instead of the expensive cuff material, of a film material, which is likewise fluid-tight, differs therefrom and may possibly be markedly more favorable. The cost of manufacturing the sphygmomanometer cuff is advantageously reduced in this manner as well. This is especially desirable when the sphygmomanometer cuff shall be, for example, a part of a disposable set or is used as a disposable product itself.

Sphygmomanometer cuffs manufactured by means of the process according to the present invention are likewise covered by the present invention without any further explanation. The advantages that can be gained in this connection correspond to those already mentioned in the discussion of the process.

The person skilled in the art will recognize that not only sphygmomanometer cuffs according to the present invention can be manufactured by means of the process in accordance with claims. Conventional sphygmomanometer cuffs as well as generally sphygmomanometer cuffs not according to the present invention, which do not have all the features of the claimed sphygmomanometer cuffs, can also be advantageously manufactured by means of the process in accordance with the invention.

The sphygmomanometer cuff according to the present invention, as was discussed above, or a sphygmomanometer cuff which is manufactured according to the process discussed above, is used to measure the blood pressure of a patient.

By using such a sphygmomanometer cuff, the blood pressure of the patient can be determined with the advantages mentioned above in a simple and at the same time reliable manner with reduced errors of measurement. The blood pressure values measured in this manner can be used, so to speak, as interim results together with other physiological parameters, symptoms, disease symptoms and taking into account data from the case history, clinical surveys and bearing phenomena such as the so-called white coat symptom in mind, for a diagnosis, such as essential hypertension, shock or the like.

As was discussed above, the sphygmomanometer cuff according to the present invention or a sphygmomanometer cuff that is manufactured according to one of the processes discussed above, is used, furthermore, to measure a blood pressure while determining the width of the inflatable cuff part of the sphygmomanometer cuff being used for the blood pressure measurement on the upper arm, which width is to be used, based on the length of the patient's upper arm.

According to another aspect of the invention, a method is provided for measuring blood pressure. The method comprises the step of providing a cuff structure including an inflatable cuff part for being filled with a fluid for exerting pressure on the blood vessel. The inflatable cuff part has a first width at a first region or point along a longitudinal direction of the inflatable cuff part and has a second width at a second region or point along the longitudinal direction of the inflatable cuff part. The cuff structure is applied over a blood vessel of a body part including rotating the sphygmomanometer cuff in the circumferential direction relative to the body part such that a selected region of the inflatable cuff part, with a selected width, is over the blood vessel.

The method may advantageously further include measuring a dimensional aspect of the body part to determine the selected portion of the inflatable cuff part that comes to lie over the blood vessel. The applicant was able to determine that the procedure commonly used hitherto to determine the particular suitable size of a sphygmomanometer cuff on the basis of the circumference of the upper arm may lead to incorrect measurement of the blood pressure. This can be explained by the fact that the circumference of the upper arm of men is frequently different from the corresponding circumference in women of equal height, and that, furthermore, there also are differences in the upper arm circumference between patients with and without physical exercise. Furthermore, it was observed that the rule according to which the height or width of the inflatable cuff part with which pressure is to be exerted on the vessel shall be 40% of the upper arm circumference may possibly be correct in adults but often does not apply in children and senior citizens or geriatric patients.

To increase the correctness of the blood pressure measurement, the applicant therefore proposes to use the length of the upper arm rather than the circumference of the upper arm as a reference to determine the correct width or height of the inflatable cuff part for measuring the blood pressure on the upper arm. The length of the upper arm can be determined, for example, easily by palpating the acromion and the radius in the elbow region and measuring the distance between the two. This procedure advantageously rules out, for example, the effect of the state of exercise of a physically active human being on the measurement result. The measuring inaccuracies discussed above, which occur in children and senior citizens as well as measuring inaccuracies occurring between the sexes, are likewise reduced or even avoided.

Measurement carried out in such a way that the length of the upper arm is taken into account is possible not only with the above-described sphygmomanometer cuff according to the present invention or with a sphygmomanometer cuff manufactured according to the process according to the present invention. Measurement carried out in such a way that the length of the upper arm is taken into account is rather possible advantageously with conventional sphygmomanometer cuffs as well.

The present invention will be explained in more detail with reference to the drawings attached, identical reference numbers designating identical structures. The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which preferred embodiments of the invention are illustrated.

BRIEF DESCRIPTION OF THE DRAWINGS

In the drawings:

FIG. 1A is an internal side view of a sphygmomanometer cuff according to the present invention;

FIG. 1B is an external side view of a sphygmomanometer cuff according to the present invention;

FIG. 2A is an internal side view showing a different design of the sphygmomanometer cuff according to the present invention;

FIG. 2B is an external side view showing the design of the sphygmomanometer cuff of FIG. 2A;

FIG. 3A is an internal side view showing a different design of the sphygmomanometer cuff according to the present invention;

FIG. 3B is an external side view showing the design of the sphygmomanometer cuff of FIG. 3A;

FIG. 4A is an internal side view showing a different design of the sphygmomanometer cuff according to the present invention;

FIG. 4B is an external side view showing the design of the sphygmomanometer cuff of FIG. 4A;

FIG. 5A is an internal side view showing a different design of the sphygmomanometer cuff according to the present invention;

FIG. 5B is an external side view showing the design of the sphygmomanometer cuff of FIG. 5A;

DESCRIPTION OF THE PREFERRED EMBODIMENTS

Figure 6:
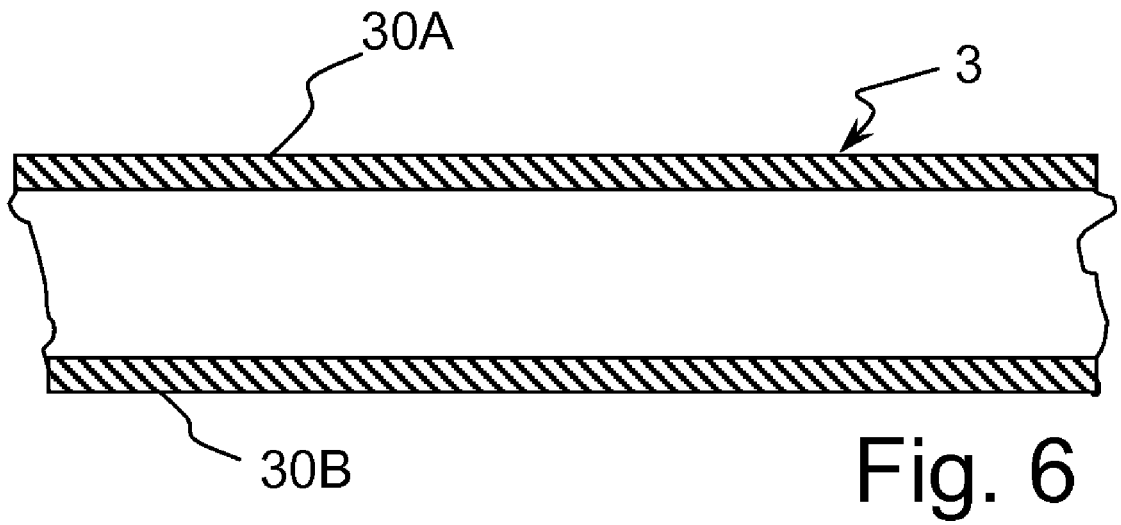
FIG. 6 is a sectional view of two material layers that are connected in a fluid-tight manner to form at least one inflatable cuff part, which has different widths or to form several inflatable cuff parts, each which has one of several different widths.

Referring to the drawings in particular, FIGS. 1A and 1B show a sphygmomanometer cuff 1 according to the present invention, which is shown in an external view in FIG. 1A and in an internal view in FIG. 1B. It can be clearly recognized that the area of the sphygmomanometer cuff 1, which area comprises the inflatable cuff part 3, rises conically upward corresponding to the base shape. The inflatable cuff part 3, can be filled by means of the flexible tube connection 5.

In the external view in FIG. 1A, the sphygmomanometer cuff 1 has, furthermore, hook strips 7 of a hook and loop closing device, which is divided into different individual strips (four hook strips in FIG. 1A forming four closing means) for the advantageous reasons discussed above.

The pad strips (loop strips) 9, which belong to the hook strips 7 (to form the four closing means discussed above) and which make possible the closing of the sphygmomanometer cuff 1 together with the hook strips 7, for example, around the upper arm of the patient, are recognized in FIG. 1B. In FIG. 1B the sphygmomanometer cuff 1 according to the present invention is shown as an internal view or view from the inside (interior side). The pad strips 9 are also not designed, unlike in the state of the art, as a continuous pad strip, but as 12 narrow pad strips 9 provided independently from one another. It is pointed out that, unlike as shown in FIG. 1, the hook strip 7 or the pad strip 9 may be made in one piece and the respective other of the latter two strips may be made as multiple-piece strips.

The sphygmomanometer cuff 1 according to FIGS. 1A and 1B has a scale 11, shown in FIG. 1B, of a length-measuring means. With the length-measuring means the length of the upper arm or the circumference of the upper arm or even the length or the circumference of another body part can be measured.

The sphygmomanometer cuff 1 is put on according to the present invention as a function of the circumference or length determined by means of the scale 11 of the length-measuring means such that the identical value (corresponding value) of an index line for the vessel, hereinafter called the blood vessel markings 13, will come to lie over the corresponding vessel or artery.

FIGS. 2A, 2B, 3A, 3B, 4A, 4B, 5A and 5B show four possible designs of the sphygmomanometer cuff 1 according to the present invention. FIGS. 2A, 3A, 4A, and 5A depict the external view or exterior surface view. FIGS. 2B, 3B, 4B and 5B depict the corresponding internal view or interior side view.

The sphygmomanometer cuff 1 according to each of FIGS. 2A, 2B, 3A, 3B, 4A, 4B, 5A and 5B has a cuff section 15 as well as a cuff section 17, the cuff section 17 corresponding to the inflatable cuff part 3. Section 15 has no inflatable cuff part and is used essentially only to close and hold the sphygmomanometer cuff 1 and especially the inflatable cuff part 3 in the desired position. The cuff section 17 is surrounded by a weld seam 19, as a result of which the inflatable cuff part 3 is formed. As can be determined from all four designs according to FIGS. 2B, 3B, 4B and 5B (the internal views), the left-side area 21 of the cuff section 17 converges conically, unlike the remaining right-side area 23 (areas 21 and 23 are shown purely graphically (separately by broken lines in FIG. 2B)). This is explained by the fact that about 25% of the extension of the inflatable cuff part, which should not be used for blood pressure measurement, lie in the right-side area 23. It is thus ensured that a middle area of the inflatable cuff part will lie over the blood vessel, and the pressure, which is generated by the inflation of the sphygmomanometer cuff 1, can therefore also act with certainty on the vessel. The outer 25% of the inflatable cuff part 3 in the longitudinal or circumferential direction are usually not used, for this reason, for applying pressure on the vessel. Correct seating of the inflatable cuff part 3 over the vessel is possible by means of orientation to the markings 13 for the artery on the sphygmomanometer cuff 1, as is shown in FIG. 1B. The same type of the markings 13 for the artery on the sphygmomanometer cuff 1 is provided for each of the four designs according to FIGS. 2B, 3B, 4B and 5B but is omitted to not overcrowd the Figures.

To make better handling of the sphygmomanometer cuff 1 possible and to prevent stress for the patient due to the needlessly broad sphygmomanometer cuff 1, namely, in an area which is not used for the blood pressure measurement anyway, as was explained above with reference to the outer 25%, the conical rise of the inflatable cuff part 3 in the transition to the right-side area 23 of the internal view in FIGS. 1A and 1B is interrupted. The inflatable cuff part 3 thus ends at right angles in the right-side area 23.

In FIGS. 5A and 5B a sphygmomanometer cuff 1 of a symmetrical design is shown. In another advantageous embodiment of the sphygmomanometer cuff 1 according to the present invention, the flexible tube connection 5 may also be provided, for example, as a plug-type or plug-in solution on both sides, i.e., both at the bottom relative to the showing in FIGS. 2A, 2B, 3A, 3B, 4A, 4B, 5A and 5B and at the top, i.e., also opposite the flexible tube connection 5 shown. This makes possible the simplified use and operation of the sphygmomanometer cuff 1, which was discussed above, especially also from the head side of the patient during an operation.

FIGS. 2A, 2B, 3A, 3B, 4A, 4B, 5A and 5B show, furthermore, the conical shape of the inflatable cuff part 3, which imparts different heights or widths to the inflatable cuff part 3. Two of these different widths are marked by I-I and II-II. Additional areas of a respective different width are located between these widths. These are coordinated with the blood vessel markings 13.

The present invention proposes a sphygmomanometer cuff 1 for measuring the blood pressure over a blood vessel, wherein the sphygmomanometer cuff 1 has at least one inflatable cuff part 3, which can be filled with a fluid for exerting pressure on the blood vessel, the inflatable cuff part 3 having different widths at at least two points along its longitudinal direction.

Figure 7:
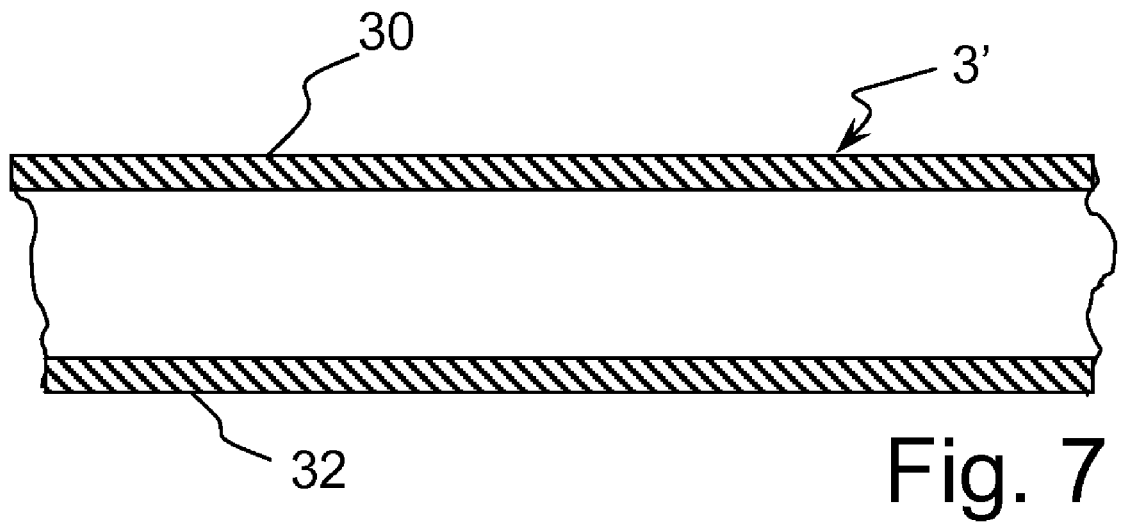
FIG. 7 is a sectional view of two material layers, including a film layer, that are connected in a fluid-tight manner to form at least one inflatable cuff part, which has different widths or to form several inflatable cuff parts, each which has one of several different widths.

The present invention proposes, furthermore, a process for manufacturing a sphygmomanometer cuff, with the step of assembling two material layers 30A, 30B in a fluid-tight manner, such that at least one inflatable cuff part 3, which has different widths at, at least two points along its longitudinal direction, is formed between the material layers 30A, 30B (FIG. 6). In an especially preferred embodiment of the process according to the present invention, an inflatable cuff part 3' is limited by a cuff material 30 as well as a film material 32, which differs therefrom, and is designed in this manner (FIG. 7). A double layer (30A, 30B) of the cuff material 30, i.e., of the material of which the inflatable cuff part is manufactured, may be absent here altogether. The inflatable cuff part 3' may be provided wherein the second layer of material needed to complement the inflatable cuff 3' part may consist, instead of the expensive cuff material 30, of the film material 32, which is likewise fluid-tight, differs therefrom and may possibly be markedly more favorable.

The sphygmomanometer cuff 1 according to the present invention or a sphygmomanometer cuff which is manufactured according to the above-described process is used according to the method described above. The method involves measuring a blood pressure of a patient while determining the width of the inflatable cuff part 3 of the sphygmomanometer cuff being used for the blood pressure measurement on the upper arm, which said width is to be used, based on the length of the patient's upper arm or dimension of a body part.

While specific embodiments of the invention have been shown and described in detail to illustrate the application of the principles of the invention, it will be understood that the invention may be embodied otherwise without departing from such principles.

What is claimed is:

1. A sphygmomanometer cuff for measuring the blood pressure by application over a blood vessel, the sphygmomanometer cuff comprising:
   a cuff structure including an inflatable cuff part for being filled with a fluid for exerting pressure on the blood vessel and a closing device for closing the sphygmomanometer cuff around a body part, wherein said closing device comprises a plurality of individual first side closing strips on a first side of said cuff structure, each of said individual first side closing strips being spaced apart along a length of said cuff structure and being independent of an adjacent individual first side closing strip and at least one second side closing strip on a second side of said cuff structure, wherein:
   said inflatable cuff part has a first width at a first region along a longitudinal direction of the inflatable cuff part and has a second width at a second region along the longitudinal direction of the inflatable cuff part, providing a changing width along the longitudinal direction; and
   said cuff structure has a plurality of blood vessel markings with a first blood vessel mark coordinated with the first width and with a second blood vessel mark coordinated with the second width.

2. A sphygmomanometer cuff in accordance with claim 1, wherein said inflatable cuff part has at least one conical section.

3. A sphygmomanometer cuff in accordance with claim 1, wherein said cuff structure has length-measuring markings with a scale for length and/or circumference measurement.

4. A sphygmomanometer cuff in accordance with claim 1, wherein said cuff structure further comprises a non-inflatable cuff part connected to said inflatable cuff part, said non-inflatable cuff part having a conical section providing a changing width along the longitudinal direction.

5. A sphygmomanometer cuff in accordance with claim 1, wherein said cuff structure has an axially symmetrical shape.

6. A sphygmomanometer cuff in accordance with claim 1, wherein said inflatable cuff part is limited by a cuff material portion and a film material portion that is different from said cuff material portion.

7. A sphygmomanometer cuff in accordance with claim 4, wherein said inflatable cuff part is formed between two layers of cuff material, wherein said non-inflatable cuff part has only one layer of cuff material.

8. A process for manufacturing a sphygmomanometer cuff, the process comprising the step of:
   forming a cuff structure including assembling two material layers in a fluid-tight manner to form an inflatable cuff part between the material layers, wherein the cuff structure is formed with a closing device for closing the sphygmomanometer cuff around a body part, wherein the closing device has a plurality of individual first side closing strips on a first side of said cuff structure, each of said individual first side closing strips being spaced apart along a length of said cuff structure and being independent of an adjacent individual first side closing strip and at least one second side closing strip on a second side of said cuff structure, wherein the inflatable cuff part is formed having a first width at a first point along a longitudinal direction of the inflatable cuff part and having a second different width at a second point along the longitudinal direction of the inflatable cuff part, providing a changing width along the longitudinal direction; and providing a plurality of blood vessel markings on the cuff structure with a first blood vessel mark coordinated with the first width and with a second blood vessel mark coordinated with the second width.

9. A process in accordance with claim 8, wherein the step of assembling two material layers in a fluid-tight manner forms the inflatable cuff part with a conical section.

10. A process in accordance with claim 8, further comprising:
providing a scale mark on the cuff structure for the measurement of the length and/or circumference.

11. A process in accordance with claim 8, wherein the step of forming a cuff structure includes providing a non-inflatable cuff part connected to said inflatable cuff part, said non-inflatable cuff part having a conical section providing a changing width along the longitudinal direction.

12. A process in accordance with claim 8, wherein the cuff structure is formed with an axially symmetrical shape.

13. A process in accordance with claim 8, wherein the step of forming the cuff structure includes limiting said inflatable cuff part by a cuff material and a film material that is different therefrom.

14. A process in accordance with claim 8, wherein the step of forming the a cuff further includes forming a non-inflatable cuff part with only one layer of cuff material.

15. A sphygmomanometer cuff for measuring the blood pressure by application over a blood vessel, the sphygmomanometer cuff comprising:
a cuff structure including an inflatable cuff part for being filled with a fluid for exerting pressure on the blood vessel, said inflatable cuff part having a width that varies along a longitudinal direction of the inflatable cuff part to provide a first width at a first region along the longitudinal direction of the inflatable cuff part and a second width at a second region along the longitudinal direction of the inflatable cuff part, providing a changing width along the longitudinal direction;
a closing device for closing the sphygmomanometer cuff around a body part, said closing device comprising a first closing element on a first side of the cuff structure and a second closing element on a second side of the cuff structure; and
a plurality of blood vessel markings, each of said blood vessel markings being for use based on a corresponding length of a patient's upper arm or dimension of a body part and said blood vessel markings including a first blood vessel mark at a position along the longitudinal direction of the inflatable cuff part that is coordinated with said first width and a second blood vessel mark at another position along the longitudinal direction of the inflatable cuff part that is coordinated with said second width.

16. A sphygmomanometer cuff in accordance with claim 15, further comprising:
length-measuring markings with a scale for length and/or circumference measurement, wherein the length-measuring markings indicate a corresponding one of said blood vessel markings to be used based on a length and/or circumference measurement.

17. A sphygmomanometer cuff in accordance with claim 16, wherein:
said first closing element is one of a plurality of individual first side closing strips on a first side of said cuff structure, each of said individual first side closing strips being spaced apart along a length of said cuff structure and being independent of an adjacent individual first side closing strip; and
said second closing element is one of a plurality of second side closing strips on a second side of said cuff structure, each of said individual second side closing strips being spaced apart along a length of said cuff and being independent of an adjacent individual second side closing strip wherein individual first side closing strips are connected to individual second side closing strips for closing the sphygmomanometer with a selected width to provide the selected width at a desired position relative to a blood vessel.

18. A sphygmomanometer cuff in accordance with claim 1, wherein:
said closing device has a plurality of second side closing strips on the second side of said cuff structure, each of said individual second side closing strips being spaced apart along the length of said cuff structure and being independent of an adjacent individual second side closing strip wherein individual first side closing strips are connected to individual second side closing strips for closing the sphygmomanometer.

19. A process in accordance with claim 8, wherein:
the closing device has a plurality of second side closing strips on the second side of said cuff structure, each of said individual second side closing strips being spaced apart along the length of said cuff structure and independent of an adjacent individual second side closing strip wherein individual first side closing strips are connected to individual second side closing strips for closing the sphygmomanometer.

* * * * *